(12) United States Patent
Jung et al.

(10) Patent No.: US 9,974,614 B2
(45) Date of Patent: May 22, 2018

(54) DRIVE AND AUXILIARY DEVICE FOR ULTRASOUND CLEANING APPARATUS

(71) Applicant: BANDELIN patent GmbH & Co. KG, Berlin (DE)

(72) Inventors: Rainer Jung, Berlin (DE); Jonas Möhricke, Berlin (DE)

(73) Assignee: BANDELIN patent GmbH & Co. KG, Berlin (DE)

( * ) Notice: Subject to any disclaimer, the term of this patent is extended or adjusted under 35 U.S.C. 154(b) by 691 days.

(21) Appl. No.: 14/459,148

(22) Filed: Aug. 13, 2014

(65) Prior Publication Data

US 2015/0047678 A1   Feb. 19, 2015

(30) Foreign Application Priority Data

Aug. 16, 2013  (DE) .................... 20 2013 007 537 U
Aug. 16, 2013  (EP) ..................... 13180744
Dec. 20, 2013  (EP) ..................... 13199128

(51) Int. Cl.
| | |
|---|---|
| A61B 90/70 | (2016.01) |
| B08B 9/035 | (2006.01) |
| B08B 9/032 | (2006.01) |
| A61B 19/00 | (2006.01) |
| B08B 3/12 | (2006.01) |

(52) U.S. Cl.
CPC .............. *A61B 19/34* (2013.01); *A61B 90/70* (2016.02); *B08B 3/123* (2013.01); *A61B 2090/701* (2016.02); *Y10T 74/20* (2015.01)

(58) Field of Classification Search
CPC ......... B08B 3/123; Y10T 74/20; A61B 19/34; A61B 90/70; A61B 2090/701
See application file for complete search history.

(56) References Cited

U.S. PATENT DOCUMENTS

| | | | | |
|---|---|---|---|---|
| 5,711,921 | A | 1/1998 | Langford | |
| 5,713,452 | A * | 2/1998 | Halsted | B65G 23/44 198/370.07 |
| 5,921,256 | A * | 7/1999 | Barin | A61B 90/70 134/104.2 |
| 6,162,395 | A * | 12/2000 | Kowanko | A61B 1/125 422/28 |
| 6,286,527 | B1 * | 9/2001 | Stanley | A01N 37/16 134/169 C |
| 2007/0234494 | A1 * | 10/2007 | Suzuki | A61B 1/122 15/104.2 |

(Continued)

FOREIGN PATENT DOCUMENTS

| | | |
|---|---|---|
| DE | 10248460 A1 | 4/2004 |
| WO | 2012098732 A1 | 7/2012 |
| WO | 2012148266 A1 | 11/2012 |

*Primary Examiner* — Michael Barr
*Assistant Examiner* — Benjamin L Osterhout
(74) *Attorney, Agent, or Firm* — Studebaker & Brackett PC (57) ABSTRACT

The application discloses an auxiliary device for a tank of an ultrasound apparatus which comprises a rack and at least one adapter for a medical instrument.

Thereby, the adapter comprises a housing and at least one coupling element which is movable with respect to the housing by way of a drive and which can be coupled to the medical instrument, so that a movement of the coupling element effects an active movement of at least one region of the medical instrument.

15 Claims, 8 Drawing Sheets

(56) References Cited

U.S. PATENT DOCUMENTS

| | | | |
|---|---|---|---|
| 2009/0119856 A1* | 5/2009 | Onishi | A61B 90/70 15/104.066 |
| 2009/0146032 A1* | 6/2009 | Bettenhausen | A61B 50/34 248/220.31 |
| 2009/0217956 A1* | 9/2009 | Noguchi | A61B 1/123 134/57 R |
| 2011/0132404 A1 | 6/2011 | Lutz et al. | |
| 2012/0085720 A1* | 4/2012 | Bettenhausen | A61L 2/26 211/85.13 |
| 2013/0186428 A1* | 7/2013 | Lutz | B08B 3/12 134/1 |
| 2013/0298945 A1 | 11/2013 | Yamamoto et al. | |
| 2013/0333125 A1* | 12/2013 | Majeed | A61B 1/123 15/21.1 |

\* cited by examiner

DRIVE AND AUXILIARY DEVICE FOR ULTRASOUND CLEANING APPARATUS

This application claims priority of European Patent Application EP 13 180 744.8 filed on Aug. 16, 2013, entitled "Zusatzvorrichtung für Ultraschall-Reinigungsgeräte, Steuerund/oder Bedienvorrichtung für ein Ultraschallgerät, sowie Verfahren zur aktiven Bewegung zumindest eines Bereichs eines medizinischen Instruments", European Patent Application EP 13 199 128.3 filed on Dec. 20, 2013, entitled "Antrieb und Zusatzvorrichtung für Ultraschall-Reinigungsgeräte", and German Utility Model Application DE 20 2013 007 537.6 filed on Aug. 16, 2013, entitled "Antrieb und Zusatzvorrichtung für Ultraschall-Reinigungsgeräte", all of which are hereby incorporated by reference herein in their entirety.

The invention relates to an auxiliary device for an ultrasound apparatus or an ultrasound cleaning apparatus, to a control and/or operating device for an ultrasound cleaning apparatus with such an auxiliary device, as well as to a method for the active movement of at least one region of a medical instrument in an ultrasound cleaning apparatus.

On cleaning medical instruments by way of low-frequency ultrasound, foreign particles on or on medical instruments are detached due to specific ultrasound active mechanisms (such as cavitation, micro streaming, jet-formation, etc.)

Hereby, in particular, surgical instruments are placed into a basket and subsequently introduced into a through of an ultrasound cleaning apparatus which is filled with a fluid. Subsequently, the tank (trough) is subjected to ultrasound, so that foreign particles and attachments can detach within a short time. Optionally, this process is supported by the addition of suitable cleaning preparations and/or disinfection preparations which are added to the fluid.

A further use is known from the field of laparoscopy. Hereby, foreign particles not only can occur on the outer side of the instrument, but also in a lumen of the shank. Devices such as the product Sonomic of BANDELIN electronic GmbH & Co. KG are known, in order here to develop a cleaning effect. With this product, an adapter is attached onto the distal end of the shank, and this permits fluid to be pulled from the proximal to the distal end of the shank, so that the effect of the ultrasound can also takes its course in the inside of the shank lumen.

Basically, such a cleaning technology can also be applied with instruments from the field of robot-supported, minimal invasive surgery, such as for example the Endo-Wrist® products of the daVinci system of Intuitive Surgical Inc. These instruments mostly have more than one mechanism (mechanics), wherein a mechanism in each case effects a certain movement of the instrument, e.g. a rotation of the instrument shank, or a movement of a gripper at the distal end of the instrument shank.

However there continues to exist the need to improve the cleaning effect for medical instruments. For this, a European patent application of the same applicant has been submitted on the same day. It is the object of the present application to provide a drive for an auxiliary device.

SUMMARY

This object may be achieved by a drive according to the features of claim 1, as well as of an auxiliary device for ultrasound cleaning apparatus, according to the features of claim 14.

In an embodiment, a drive comprises at least one shaft element, which can be driven via a first force transmission element, wherein the shaft element is coupled to at least one coupling element via a second force transmission element, so that a movement can be transmitted from the shaft element onto the at least on coupling element. The second force transmission element is coupled to the at least one coupling element in a manner such that the second force transmission element transmits no movement of the shaft element onto the at least one coupling element on exceeding a predefined movement resistance of the at least one coupling element.

It is possible to ensure an active movement of medical robotics instruments in an ultrasound bath with the help of the previously described drive, without damaging a mechanism for moving individual parts of the instrument.

The instrument may be moved or rotated in the ultrasound bath in a manner such that a part-element of the coupling element is engaged with the mechanism of the instrument, and thus a movement of the coupling element is transmitted onto the instrument. As soon as the mechanism of the apparatus has come to an abutment, the mechanism of the instrument exerts a movement resistance which can only be overcome by way of applying a very high force. However, this very high force would lead to a damage of the mechanism of the instrument. The exerted movement resistance of the mechanism of the medical instrument leads to a movement resistance of the coupling element, i.e. the coupling element is prevented from a further rotational movement by way of the mechanism of the instrument. The resistance between the second force transmission element and the coupling element is selected in a manner such that this is lower than the movement resistance effected by the mechanism of the instrument. If a mechanism of the instrument thus reaches the abutment, the respective coupling element is subjected to a movement resistance, and a movement of the shaft element is no longer transmitted onto the coupling element. Thus the instrument or part thereof can be actively moved, the mechanism of the instrument is protected and the instrument can be well cleaned without inhibiting its functionality.

In a further embodiment example, a first and a second coupling element is coupled in each case via a second force transmission element to a shaft element, so that a first coupling element can move independently of the second coupling element. In this manner, it is not important for the distal, movable end of the instruments to be situated in a predefined position before the insertion into an adapter, since the movement of the coupling elements are decoupled from one another. In the case that the drive is designed in a manner such that more than one coupling element for coupling in each case to one mechanism of the instrument is present, the coupling elements can be driven by a preferably single drive, in a manner such that a first coupling element which has moved a first mechanism of the instrument onto the abutment no longer transmits a movement onto the first mechanism, and a second coupling element which moved a second mechanism of the instrument, continues to keep this mechanism in motion. In other words, the first and a second (or also further) coupling elements, independently of one another, but simultaneously can transmit a movement onto a first and second mechanism of the instrument respectively, wherein the force transmission elements coupled to the coupling elements are simultaneously driven by a single drive. For example, in each case a slip coupling can be arranged between the force transmission elements and the coupling elements. Simultaneously here is to be understood in that the first as well as the second coupling element in each case can move a first and second mechanism coupled to the first and second coupling element respectively, at the same time. A slip coupling engages when one of the first or second mechanisms gets to the abutment, and subsequently it is only the mechanism which has not yet gotten to the abutment which is moved. Preferably, the drive is configured in a manner such that more than one mechanism of an instrument, and more than one instrument can be moved, i.e. a single drive moves two or more instruments, wherein one or more than one mechanism of the two or more instruments can be simultaneously moved. Moreover, the movement of the mechanisms is effected independently of one another, i.e. whereas a mechanism which has come to the abutment is no longer moved, the further mechanisms which have not yet got to their abutment can continue to be moved by the drive.

In further embodiments, belts, for example toothed belts or round belts of plastic, artificial material or rubber can be applied as force transmission elements. Further embodiments are to be found in the claims.

With the drive mentioned here, it may be possible to implement a method for the control of the drive, with which the drive is driven firstly for a first time period in a first direction, and subsequently for a second time period in a second direction which is opposite to the first direction. The length of the time period amongst other things may be selected in dependence on the speed at which the drive drives the coupling element. Since a mechanism of the instrument has a maximal movement region, the first and the second time period are selected in a manner such that this is longer than the time, in which a mechanism driven by a coupling element runs through the maximal movement region. In this manner, within a time space of the first and second time period, one succeeds in all mechanisms driven by a coupling element having got to an abutment. In the case that all parts of a mechanism which are coupled to a coupling element in each case have an identical movement region (in the sense of distance), i.e. movement length, a shorter time period can be set after the first and second time period, wherein the shorter time period corresponds to the length which the parts of the mechanisms require in order to run through the respective complete movement region. In the case that different mechanisms have different movement regions, i.e. the paths (stretches) of the parts which can be covered by the part of the mechanism can differ from one another, then after running through the first and the second time period, possibly a shorter time period which that mechanism with the greatest path to be covered requires for a complete movement region is to be selected. By way of this, it is possible for all parts of the mechanism to be moved over their complete movement region during the cleaning of the instruments in a cleaning bath, in particular a cleaning bath which is subjected to ultrasound, so that the cleaning effect of the fluid which can be subjected to ultrasound can act on the parts of the mechanism which are moved by the drive, in all movement conditions, and thus the cleaning effect is maximised.

The first and second time period can be selected to be equally long or of different length. Since a part of the mechanism which has got to its abutment is no longer moved by the coupling element (since the force transmission element slips through for example or a slip coupling decouples a movement of the drive onto the coupling element), further parts of the mechanism which are driven by a further coupling element can be moved up to their abutment in each case, and this being independent of whether other parts of the mechanism have already reached their abutment. The length of the following time periods for moving the drive in the first or second direction can be reduced after the first and second time period, so that a cleaning run as a whole is shortened without reducing the cleaning effect. Complicated sensor systems for ascertaining as to whether one of the moved mechanisms is already located at the abutment are not necessary and are not envisaged in some embodiment examples.

DETAILED DESCRIPTION

Aspects of the auxiliary device which are freely combinable with the features of the claims are described hereinafter.

The auxiliary device preferably comprises a rack and at least one adapter for a medical instrument. The auxiliary device is designed in a manner such that this has space in a tank of an ultrasound apparatus, preferably an ultrasound cleaning apparatus. Thereby, it is advantageous if parts of the frame project out of the tank, in order thus to ensure a simplified handling of the auxiliary device on bringing it into and out of the tank.

The adapter for the medical instrument may comprise a housing and at least one coupling element which is movable with respect to the housing and can be coupled to the medical instrument. This coupling element may be movable by way of a drive. A movement of the coupling element, with an applied medical instrument effects an active movement of at least one region of the medical instrument.

Instruments from the field of telemedicine (and further instruments) may have mechanisms by way of which it is possible to carry out certain movements of the medical instrument. Thus for example, with an endoscopic instrument, the shank and the tip can be rotated at least in a plane encompassing the rotation axis of the shank. Moreover, it is possible for the instrument itself to have gripper arms or likewise, which are rotatable in a further plane, perpendicularly to the previously mentioned plane.

The coupling element arranged in the adapter may be designed in a manner such that it can dock onto a mechanism of the medical instrument and thus a movement of the coupling element is converted into an active movement of at least one region of the medical instrument. This means that the coupling element may be designed in a manner such that a movement of the coupling element, such as for example a rotation of the shank of the medical instrument, or a movement of the distal tip of the medical instrument is effected.

The adapter can comprise recesses, webs or likewise which correspond to webs or recesses of a medical instrument, in order for the coupling element to be able to be reliably coupled onto the medical instrument, so that a movement of the coupling element is converted into an active movement of a region of the medical instrument. In this manner, one can ensure that the coupling element engages at predefined points of the medical instrument, preferably engages on mechanisms of the medical instrument which are necessary for an active movement of at least one region of the medical instrument.

On account of the active movement of the medical instrument by way of the auxiliary device, the medical instrument during the exposure of the tank to ultrasound can be actively moved, so that an improved cleaning effect is ensured in the region of the moving parts of the medical instrument. In this manner, it is ensured that the ultrasound can develop its full effect even with mechanical or moving parts of the instrument which bear closely onto one another, and foreign particles can be reliably removed from the medical instrument, even from covered part-surfaces in e.g. joints.

In one embodiment of the auxiliary device, the adapter comprises a fixation device for fixing the medical instrument. Additionally or optionally to the already mentioned recesses or webs of the adapter, one can envisage a fixation or locking device which fixes at least one further region of the medical instrument on the adapter. Thereby, the fixation is of such a nature that the coupling element of the auxiliary device engages at a point of the medical instrument which effects an active movement of a region of the medical instrument which is not fixed by the fixation device. In the case of a surgical robotics instrument, this for example can mean that the proximal end of the instrument which is connected to a robot drive for the purposes of a medical operation is inserted into the adapter and is locked by way of the fixation device. Although the proximal end of the medical instrument is fixed from now on, the coupling element of the adapter however is coupled to the proximal end of the medical instrument in a manner such that the shank as well as the instruments at the distal end of the medical instrument are actively moved by way of a movement of the coupling element.

In a further embodiment, the auxiliary device at a surface of the coupling element which faces the medical instrument comprises a groove or a web which can be brought into a mechanical positive fit with a mechanism of the medical instrument to be cleaned. If the mechanism of the medical instrument is given for example by a pin or a groove, then the groove or the web of the coupling element is designed in a manner corresponding to this. In this manner a movement of the coupling element can be transmitted directly onto the mechanism of the medical instrument.

In a further embodiment, the coupling element is mounted in a resilient manner. The coupling element can be resiliently mounted since the coupling element is preferably designed in a manner so as to engage into a mechanism of the medical instrument, but the mechanism of the medical instrument and the coupling element cannot engage into one another in every orientation to one another. The effect of this can be that on applying the medical instrument, the coupling element is firstly pressed downwards unless it is engaged to the mechanism of the medical instrument, which means that a movement of the coupling element can be converted into a movement of a region of the medical instrument. On account of the resilient mounting, firstly the coupling element can be moved so that it assumes a position, in which the coupling element engages with the mechanism of the medical instrument. This can be effected for example by way of a pin of the mechanism engaging into a groove of the adapter. Only with the engagement does a movement of the coupling element transmit on the mechanism and is thus converted into an active movement of the medical instrument. Due to the slipping of the pin into the groove, a spring effect (or a comparable effect) presses the coupling element in the direction of the medical instrument and thus effects a positive fit between a mechanism of the medical instrument and the coupling element.

In a further embodiment, the coupling element is movable by way of a drive in a manner such that this coupling element is rotated. Thereby, the drive can be designed in a manner such that the coupling element is rotated into one and subsequently into an opposite direction, in an alternating manner. However, variants with a linear movement of the coupling element with corresponding medical instruments are also possible.

In a further embodiment of the invention, the auxiliary device or the coupling element is mechanically, hydraulically or pneumatically coupled to a drive. It may be ensured that no electrical components of the drive whatsoever need to be located within the tank of the ultrasound apparatus by way of this. This simplifies the operational safety and the reliability of the auxiliary device. The coupling element can accordingly comprise mechanical, hydraulic or pneumatic gears which permit a connection to an electric motor for example.

In a further embodiment, the rack is designed in a manner such that a force-producing component of the drive which is arranged on the rack, such as an electric motor for example, is arranged outside the tank, and the at least one adapter is arranged within the tank in a manner distanced to the force-producing component. No electrical components of the drive whatsoever are subjected to the effect of ultrasound on account of this, although the medical instruments can be completely lowered into the tank. This may increase the life duration of the auxiliary device. Moreover, in the case of an electric motor for example, one can make do without safety measures which are more extensive, since no electrical components need to be introduced into the tank or into the fluid which is subjected to ultrasound.

In a further embodiment, the housing of the adapter of the auxiliary device is fixed with respect to the rack. The adapter is unmovable with respect to the rack, so that only the coupling element can be moved with respect to the rack. In this manner, it is possible to fix a part of the medical instrument and to actively move the further region of the medical instrument via the coupling element.

In a further embodiment, the auxiliary device comprises openings in the housing of the adapter, so that the fluid which is located in the tank can penetrate via the adapter to into the medical instrument. The cleaning effect on all regions of the medical instrument may be improved by way of this.

In a further embodiment, the auxiliary device is connected to a suction and/or pressure rinsing device for rinsing the medical instrument, wherein the rinsing device comprises a rinsing adapter for coupling onto the medical instrument. Numerous instruments comprise one or more lumens in a shank. It could be useful to carry out a pressure rinsing or a suction rinsing through the shank, depending on which region of the medical instrument is fixed in the adapter. A suction and/or pressure rinsing device is coupled to the medical instrument by way of a rinsing adapter for this. In further embodiments, in an alternating manner, fluid a can be sucked through the rinsing adapter or pressed through this, into the instrument. In further embodiments, it is possible to couple more than one rinsing adapter to the medical instrument, in order thus simultaneously to carry out a suction rinsing in some regions, and a pressure rinsing in other regions of the instrument.

It is possible with the help of the suction and/or pressure rinsing device, to also rinse the lumen of the medical instrument during the active movement of the medical instrument, in order thus to improve the action of the ultrasound also in the inside of the medical instrument. Hereby, a control is provided which controls the active movement of the medical instrument, which means the movement of the coupling element and/or the suction and/or the pressure rinsing device.

A further aspect of the invention relates to a control device and/or operating device for an ultrasound apparatus and which is configured for the control of the auxiliary device. The control of the control and/or operating device can thereby include a control unit and a memory unit. The control unit for example can comprise programmable field arrays, microprocessors, microcontrollers or similar devices which are designed to implement instructions, for example a program code and to effect the control of motors, pumps and likewise by way of this. The control and/or operating device may thereby be designed such that in some embodiments a regular and/or periodic movement of the at least one coupling element by way of the drive is made possible. This for example can mean that the coupling element for a predefined time space is rotated anticlockwise or is moved to the front, and for a further predefined time space is moved in the opposite direction. The instructions necessary for this can for example be stored as software in the memory unit of the control and/or operating device. With regard to the memory unit, it can be the case of a volatile or non-volatile memory. A flash memory is preferably applied.

Further programs for moving the coupling element can likewise be stored as software. The respective desired movement of the coupling element can be effected by way of this. The control and/or operating unit can comprise the drive or can be connected to an external drive arranged on the auxiliary device, by way of a data connection and/or electricity connection. For this, in one embodiment, one envisages a drive of the auxiliary device being supplied with electricity by way of a cable and a plug-in connection on the one hand by way of the control device and/or operating device and on the other hand the drive being activated by the control device.

In a further embodiment, the control and/or operating device comprises the rinsing device which can be connected via a rinsing adapter to the medical instrument. Thereby, the control device and/or operating device are configured in a manner such that this not only controls the movement course of the coupling element, but optionally for this, also the rinsing procedures of a lumen of the medical instrument. Thus for example with a movement of the coupling element in a first direction, a suction rinsing of the instrument, and with the movement of the coupling element in a second direction which is opposite to the first direction, a pressure rinsing can be initiated. Alternatively, a fluid circulation can be effected within the lumen of the medical instrument via a simultaneously applied pressure rinsing and suction rinsing which is implemented in each case via different adapters. The control and/or the operating device hereby has/have the task of coordinating the rinsing procedures and the active movement of the medical instrument to one another and thus of achieving the greatest possible cleaning effect.

In a further embodiment, the control and/or the operating device have a touch-sensitive display. Different pictograms for calling up the different functions of the control and/or operating device can be imaged on the touch-sensitive display. Thus it is possible for example to only start the rinsing device, only the active movement or both programs simultaneously. The control of the ultrasound producer for subjecting the tank to ultrasound is also carried out by the control and/or operating device. Thus the control and/or operating device can be applied for different ultrasound cleaning apparatus and their accessories. Moreover, further functionalities and/or supplements of the functionalities can be incorporated into the control device by way of an interface, so that the updating of the software and an expansion of the control is possible.

A tank with an ultrasound transducer for subjecting instruments to ultrasound, for example in an auxiliary device outlined here, on its own and in combination with the auxiliary device described here is a claimable subject matter of the application.

The ultrasound transducers thereby are arranged on the tank in a manner such that the ultrasound transducers arranged in a tank base are attached in a manner following the course of an instrument to be cleaned. The ultrasound transducers thereby can be piezo sound-generators or other ultrasound producers which are known from the state of the art. The sound transducers are arranged on the outer side of the tank and are aligned such that the sound is emitted essentially from the tank into the inside of the tank.

With regard to the arrangement of the ultrasound transducers, these in the case of an instrument extending in a straight line are placed on the tank base in a manner such that at least two or more ultrasound transducers lie preferably precisely below the robotics instrument. In the case that the auxiliary device fixes more than one instrument, the ultrasound transducers for example are arranged along several rows, wherein one row is arranged in each case below an inserted instrument. One can envisage attaching spacer devices on the auxiliary device, in order to exactly align or position the auxiliary device with respect to the tank. In the case that the instruments to be cleansed are curved, the ultrasound transducers on the tank base are likewise arranged in a manner following the course of the instrument. I.e. the geometric arrangement of the ultrasound transducers is orientated towards the geometry of the instrument to be cleaned. Preferably, at least one ultrasound transducer is placed in a manner such that this is arranged exactly below a distal unit of a robotics instrument which is to be cleaned. The cleaning of the instruments is improved compared to conventional ultrasound transducer arrangements in this manner.

In one embodiment, the tank also comprises at least one ultrasound transducer on a tank wall. This for example is arranged in a manner such that this is arranged in the region of any rinsing connections of an instrument to be cleaned. Apart from robotics instruments, other surgical instruments such as e.g. instruments for MIS (minimal invasive surgery) can be applied into the tank.

Further embodiment examples are explained by way of the following figures.

There are shown in:

FIG. 5c a detailed view of components of FIG. 5a;

Figure 1:
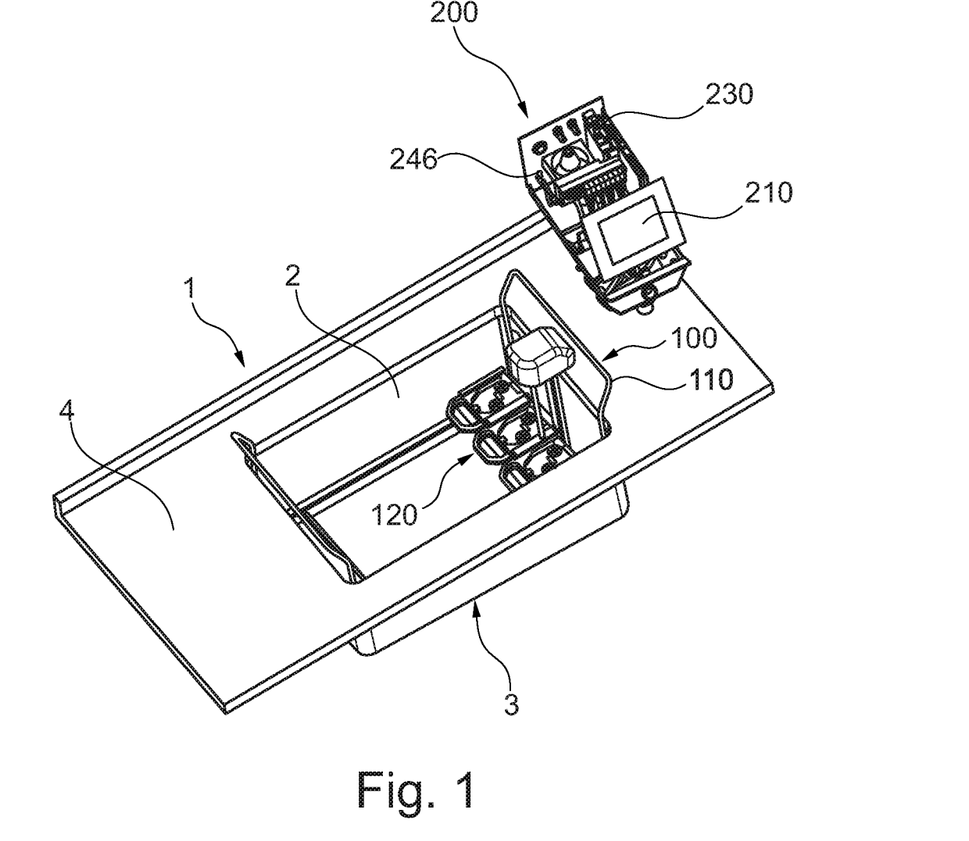
FIG. 1 a plan view of an ultrasound cleaning apparatus with an auxiliary device.

FIG. 1 shows an ultrasound cleaning apparatus 1 which comprises a tank 2 which can be filled with a fluid. Sound transmission elements (not shown) which transmit the ultrasound onto the inner walls of the tank 2 and thus transmit ultrasound waves into the fluid located in the tank 2 are located on the lower side 3 of the tank. With regard to the represented ultrasound cleaning apparatus, it is the case of an installation apparatus which is admitted into the surface of a depository 4.

An auxiliary device 100 which is explained in more detail in the subsequent figures is located in the tank 2. The auxiliary device 100 comprises a rack 110 which projects beyond the upper edge of the tank 2. An adapter bank 120 which is arranged in a manner such that this can be admitted into the tank 2 is located at the lower end of the rack 110. If the tank 2 is then filled with fluid, the fluid may completely cover the adapter bank 120 and any medical instruments which are arranged thereon.

The control and/or operating unit 200 can be connected via a cable connection to a drive of the auxiliary device. A motor of the drive is supplied with electricity as well as activated via the cable, so that this carries out movements. The control of the control and operating unit 200 is carried out by a user via the touch-sensitive display 210. Thereby, it can be the case of a capacitive or resistive touch-sensitive screen. Moreover, a pump 246 can be recognised in the representation of FIG. 1. Moreover, a control circuit board 230 with processors and memory units arranged thereon is represented.

Figure 2:
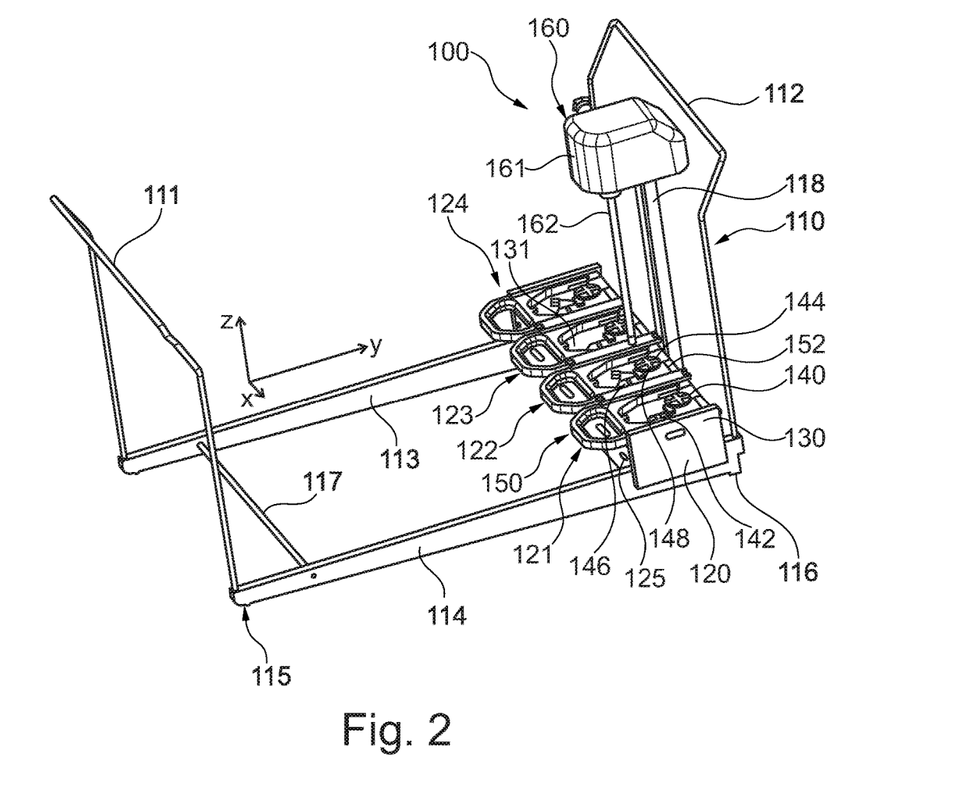
FIG. 2 a detailed view of the auxiliary device of FIG. 1.

The auxiliary device 100 without the tank 2 surrounding it in FIG. 1 is represented in FIG. 2. The rack 110 comprises two grip parts 111 and 112 which run in the x-z plane and by way of which the auxiliary device 100 can be placed out of and into the tank. Rails 113 and 114 which connect the two grip parts to one another are located at the lower end of the grips 111 and 112. Moreover, an adapter bank 120 which in the present embodiment example comprises four adapters 121 to 124 is arranged at one end of the rails 113 and 114. However, more or fewer adapters may be used in a linear configuration as shown or, for example, in a stacked configuration.

The rack 100 can be manufactured of metal and a plastic. It is also possible for example for the grips 111 and 112 to be manufactured of metal and the rails 113 and 114 of a plastic. Moreover, prominences 115 and 116 are located on the rails 113, 114, so that the rack is in contact with the tank only in a pointwise manner. The constant width of the rack is ensured via transverse struts 117.

The adapter bank 120 comprises a housing 130 which at the same time forms the housing for the four adapters 121 to 124. The housing may be manufactured of plastic and may comprise openings 125 which permit fluid located in the tank to be able to penetrate into the inside of the housing 130.

Figure 5A:
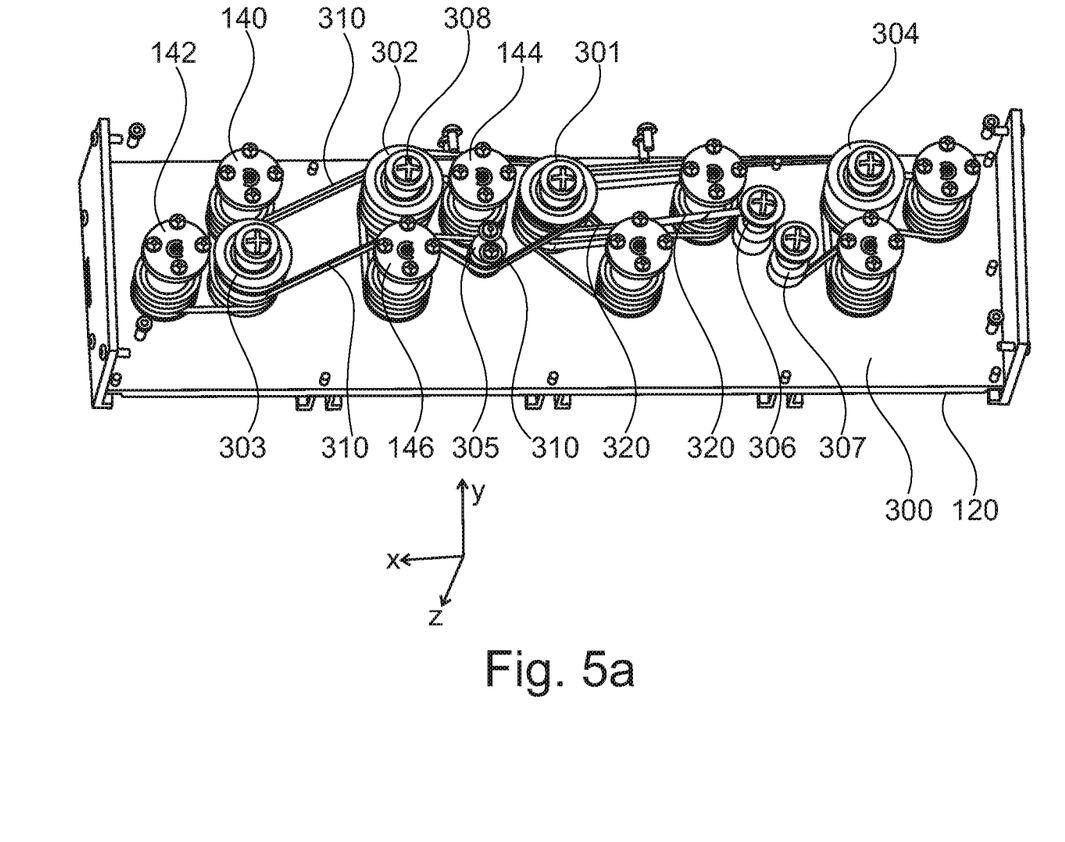
FIG. 5a a variant of a drive for an auxiliary device.

The adapter 121 comprises at least one coupling element 140 or 142 which is movable with respect to the housing. The coupling elements can be manufactured of plastic, stainless steel, titanium, other medical materials or other chemically resistant or water-resistant materials, for example, and project beyond the surface 131 of the housing 130 in the z-direction. The movable coupling elements 140 and 142 are resiliently mounted in the z-direction. The coupling elements are seated on a shaft which is not recognisable in the representation of FIG. 2 and which is driven via mechanics, hydraulics or pneumatics. The shaft is anchored on a base of the housing and comprises a spring mechanism which permits a resilience of the coupling element in the z-direction. This means that the coupling element can be pressed in the negative z-direction at least by the height, at which it projects beyond the surface 131. By way of this, it is possible for the coupling element to yield and the rotation of the coupling element to advance to such an extent that a pin arranged on a medical instrument engages into the groove of the coupling element, and thus a positive fit is produced, so that the movement of the coupling element is converted into an active movement of the medical instrument. The medical instruments are moreover fixed with a fixation device 150 at their proximal end, in the adapter bank 120. An exact alignment between the coupling elements and the mechanism of the medical instruments is given by way of this. Moreover, a drive 160 which is arranged at the upper end in the region of the grip 112 is arranged on the auxiliary device 100. This drive comprises a housing 161, in which an electric motor is arranged in this case. A coupling rod 162 which is led through an opening into the adapter bank 120 and which there via the mechanical, pneumatic or hydraulic gear 300 is coupled to the individual coupling elements (see FIG. 5) is located on the electric motor. In this manner, a rotation movement of the drive 160 amongst other things can be converted into a rotation movement of the coupling elements. The housing 161 in the present example is connected via a strut 118 to the adapter bank.

Figure 3A:
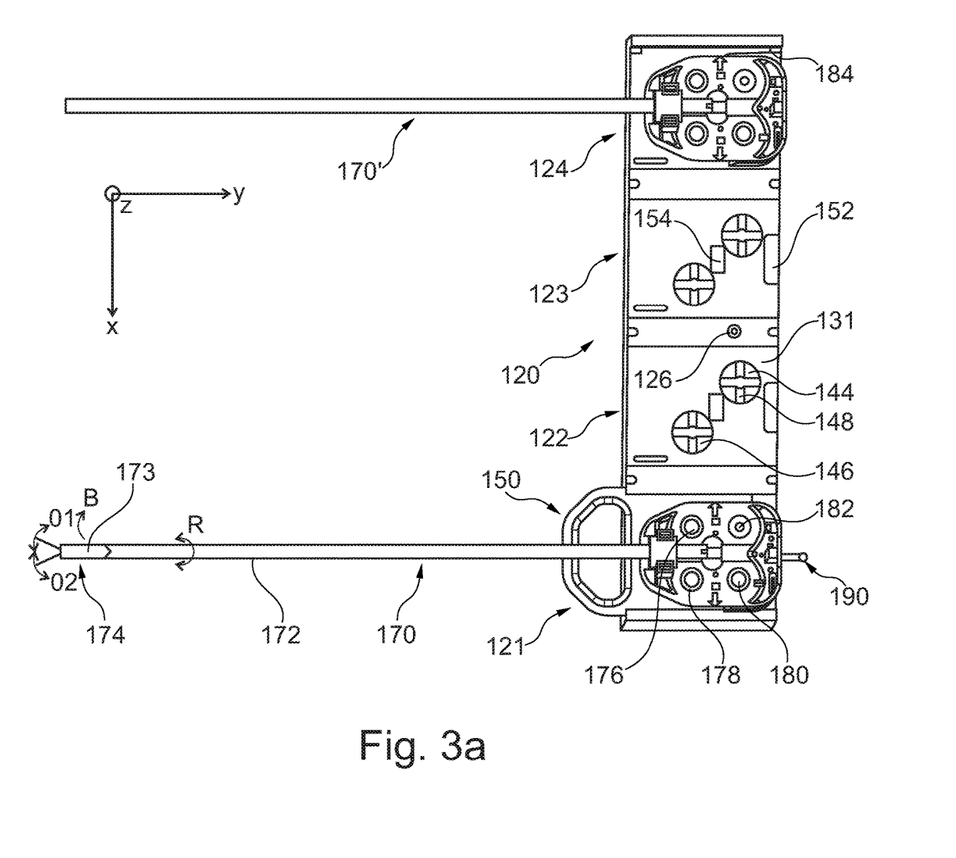
FIG. 3a a further detailed view of the auxiliary device of FIG. 1.

A view of the adapter bank of FIG. 1 and FIG. 2 in the x-y plane or represented in FIG. 3a. Apart from the adapter bank 120, a fixation device 150 as well as two medical instruments 170 and 170' are also to be seen, so that the interaction between the instrument 170 and the coupling elements can be explained in more detail. The instrument 170 comprises a shank 172 which is rotatable along the axis of the shank in the direction R. The shank 172 moreover comprises a movable tip 173 at its distal end and this tip is rotatable in the y-z plane in the direction B. Two arms of a clamp 174 are located on the tip 173, and these can be individually opened and closed in each case, wherein one arm is moved in each case in the x-y plane in a direction O1 and O2. At its proximal end, the instrument comprises a (sectioned in this view) housing which amongst other things comprises four mechanisms 176, 178, 180 and 182. Thereby, a rotation of the element 176 effects an opening in the direction O2, the mechanism 180 a rotation in the direction O1, the element 178 a rotation in the direction R and the element 182 a rotation in the direction B. In the embodiment example represented here, each of the adapters of the adapter bank 120 comprises two movable coupling elements 144 and 146 which in each case comprise two grooves 148 running to one another in a cross-like manner. The grooves thereby are selected in a manner such that a pin located on the underside of the mechanisms 176 to 182 and which is not represented, can be held in the groove 148 with a positive fit. As soon as the pin is positively held in the groove 148, a movement of the coupling element 144 for example is converted into a movement of the mechanism 182 and thus an active movement of the tip 173 in the direction B. The mechanisms can be rotated in each case past a movement region, i.e. a certain length, in order to get from a first to a second abutment. The first and second abutment corresponds to the extreme positions of that part of the instrument which is moved by the mechanism.

As already mentioned with regard to FIG. 2, the coupling elements 140, 142, 144 and 146 project slightly beyond the surface 131 in the z-direction. If now the medical instrument 170 is applied in the adapter, the pins on the lower side of the mechanism of the medical instrument firstly press on the region of the coupling element 144 and 146 which delimits the grooves. The coupling element is pressed downwards in the z-direction by way of this. With a rotation of the coupling element, the pin of the mechanism now slips along the surface delimiting the grooves 148 until this pin engages into one of the grooves. The pressure on the resiliently mounted coupling element 144 is reduced by way of this, and the coupling element is pushed upwards in the positive z-direction. The positive fit between the groove and the pin of the medical instrument is created by way of this.

Although only two coupling elements are present per medical instrument in the embodiment example shown here, in further embodiments, also less, which is to say one, or more coupling elements, which is to say three or four can be present, in order to actively create all movements of the distal region of the medical instrument. Thereby, the movement of the distal part of the medical instrument can be of such a nature such that the coupling element 144 firstly is moved about a certain angle in the clockwise direction and subsequently by the same angle in the anticlockwise direction. An active movement is transmitted onto the medical instrument by way of this, so that the distal tip 173 can be bent over an angular region of 180° for example, and the arms of the clamp can be moved over a region of likewise almost 180°.

The grooves 148 amongst other things also serve for the fixation of the medical instrument. In other embodiments, holes or webs can also assume the function of the grooves. The shape of the fixation element which is arranged on the coupling element thus depends essentially of the mechanisms of the medical instruments. If the medical instruments have pins, then grooves or holes are to be preferred. If these have holes or grooves, then webs or pins are used on the moving coupling element.

Apart from the grooves, each adapter may yet comprise fixation aids. Thus for example a relief 152 is present which is admitted into the surface 131. With the represented medical instrument, electrical contacts which project slightly beyond the lower side of the medical instrument are located in this region. These can be aligned in the relief 152, so that the positioning of the medical instrument in the adapter is simplified. Moreover, a web 154 is present which likewise engages into a corresponding relief of the lower side of the medical instrument. The fixation device 150, as is recognisable in FIG. 3b, further comprises a locking lug 158 which engages into a corresponding relief of the medical instrument. Moreover, the fixation device 150 comprises an undercut 160 which positively connects to a projection 184 of the medical instrument. In this manner the medical instrument 170 fixed in the adapter 121 is fixed in its alignment with respect to the adapter 121. Merely the coupling via the coupling element 144 and 146 and the corresponding mechanism 178 and 182 respectively effects an active movement of the distal end of the medical instrument. Further parts or regions of the medical instrument are not moved by the coupling elements.

Figure 3B:
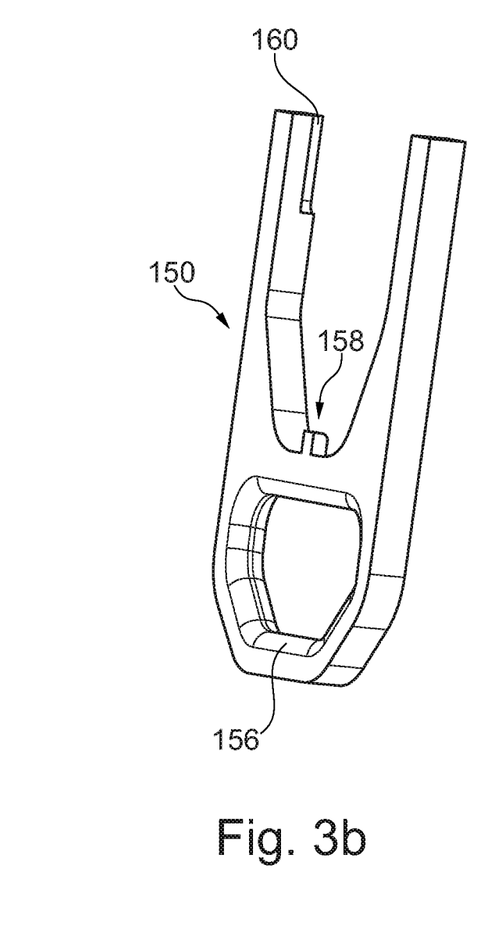
FIG. 3b an example of a fixation device of an adapter.

The fixation device 150 moreover comprises a grip 156 which when pulled in the negative y-direction, releases the medical instrument 170. This condition is to be recognised for example in the adapter 124. In further embodiment examples, the fixation element 150 comprises an abutment, so that this can only be pulled for example out of the adapter by half the length of this and subsequently remains in the adapter. A detachment of the medical instrument from the adapter is also possible in this position. The adapter housing 130 as well as the coupling element 144, 146 and the gear line which is not shown in more detail and which is seated in the housing 130, can be manufactured or of plastic or metal. The fixation device 150 can likewise be manufactured of plastic or metal.

Figure 4:
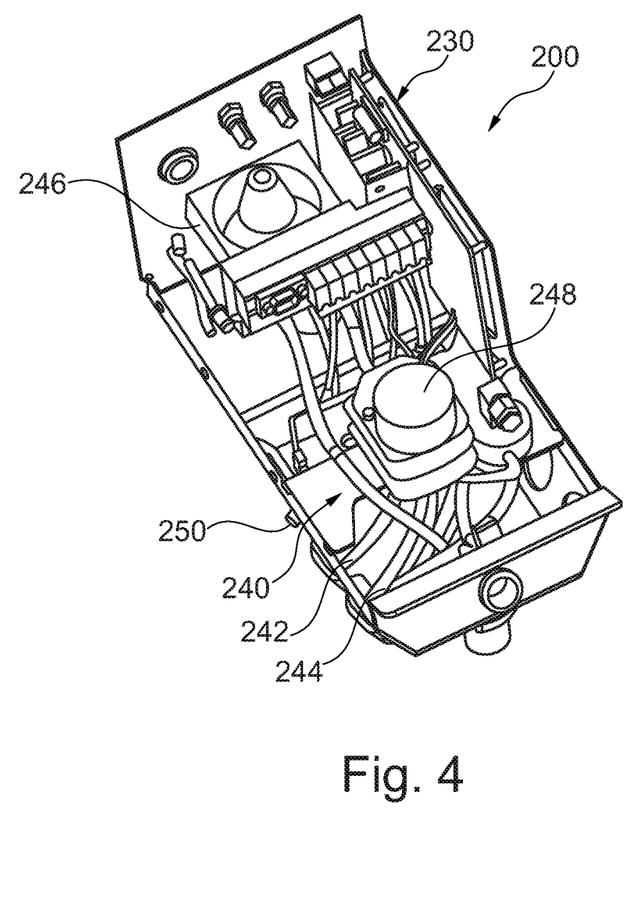
FIG. 4 a control unit and rinsing device of an opened control and/or operating unit.

The control and/or operating device 200 is represented without an upper cover and the touch-sensitive display in FIG. 4. Apart from a control circuit board 230, a rinsing device 240 can be recognised, which comprises hoses 242/244 for a suction rinsing and/or a pressure rinsing. The hoses or rather the rinsing fluid which is located therein is sucked or pressed by way of a pump 246. The hoses 242 and 244 can for example be coupled to the rising adapter 190 which is represented in FIG. 3a (which is connected to the medical instrument 170) and which connects the lumen of the shank 172 to the hose. Subsequently, a program which permits a pressure or suction rinsing of the lumen of the shank 172 can be initiated via the touch-sensitive display.

The control 230 is programmed in a manner such that the single pump 246 can subject all four instruments located in the adapter bank 120 to a suction rinsing a or pressure rinsing. Hereby, the sucking or pressing can be carried out in a channel-wise manner, which is to say one adapter after the other, so that at least for the suction rinsing, one can ascertain whether the lumen of the shank of the medical instrument is blocked or not. The switching between the suction and pressure operation is carried out by a suction change-over switch and/or pressure change-over switch 248. The channel change-over, i.e. the channel-wise subjection takes place in a channel change-over switch which is not represented. The blockage can thereby be determined via the flow passing through the pump or the pressure which thus entails. This technology to some extent is also applied in the products Sonomic.

As initially mentioned, the control device 230 comprises a processor and a memory unit. Different programs for moving the instrument are stored in the memory unit. Thus depending on the inserted instrument, one can select a program which defines the respective angular region of the rotation of the instrument and the coupling elements which are to be activated. These programs are initialised via the processor, and the processor assumes a control of the drive, so that this initiates the movement of the coupling elements according to the program, A connection 250 is likewise recognisable in FIG. 4, via which connection a connection can take place between the drive 160 of the auxiliary device 100 and the operating and/or control unit 200. With regard to the connection, it can be the case of a copper connection for example.

Components of the drive 160 which are arranged in the housing 120 are represented in more detail in FIG. 5a. The represented perspective view is from the lower side of the housing in the z-direction. A mechanism 300 can be recognised, which amongst other things comprises four shaft elements 301-304. Thereby, the shaft element 301 is connected directly to the coupling rod 162, so that a movement of the motor arranged in the housing 161 is transmitted directly onto the shaft element 301.

The shaft element 301 is coupled by way of a first force transmission element 310 in the form of a toothed belt, to the shaft elements 302 and 303, so that a rotational movement of the shaft element 301 in the anticlockwise direction effects a corresponding movement of the shaft elements 302 and 303. Additionally, the toothed belt is led via a deflection element 305

The shaft element 301 moreover is coupled via a further first force transmission element 320 to the shaft element 304. This force transmission element 320 is also led via deflection elements 306 and 307.

The first force transmission elements 310 and 320 in the present example are designed as toothed belts, which engage into corresponding teeth of the shaft elements 301-304. Moreover, the toothed belts are under mechanical stress which further favours the movement transmission of the shaft elements amongst one another.

In further embodiments, the first force transmission element can also be a belt without teeth. In further embodiments, the force transmission element can envisage a hydraulic or pneumatic movement transmission. Thus the teeth of the shaft elements can be designed for example similarly to turbine blades, so that fluid or air which is moved by the shaft element 301 without a (closed) channel effects a movement of the further shaft elements 302-304.

The shaft elements are designed in a cylinder-like manner and are rotatably mounted on a shaft. In the case of the shaft element 302, the shaft 308 can be recognised. For example a plain bearing or a ball bearing can be provided as a bearing.

Figure 5B:
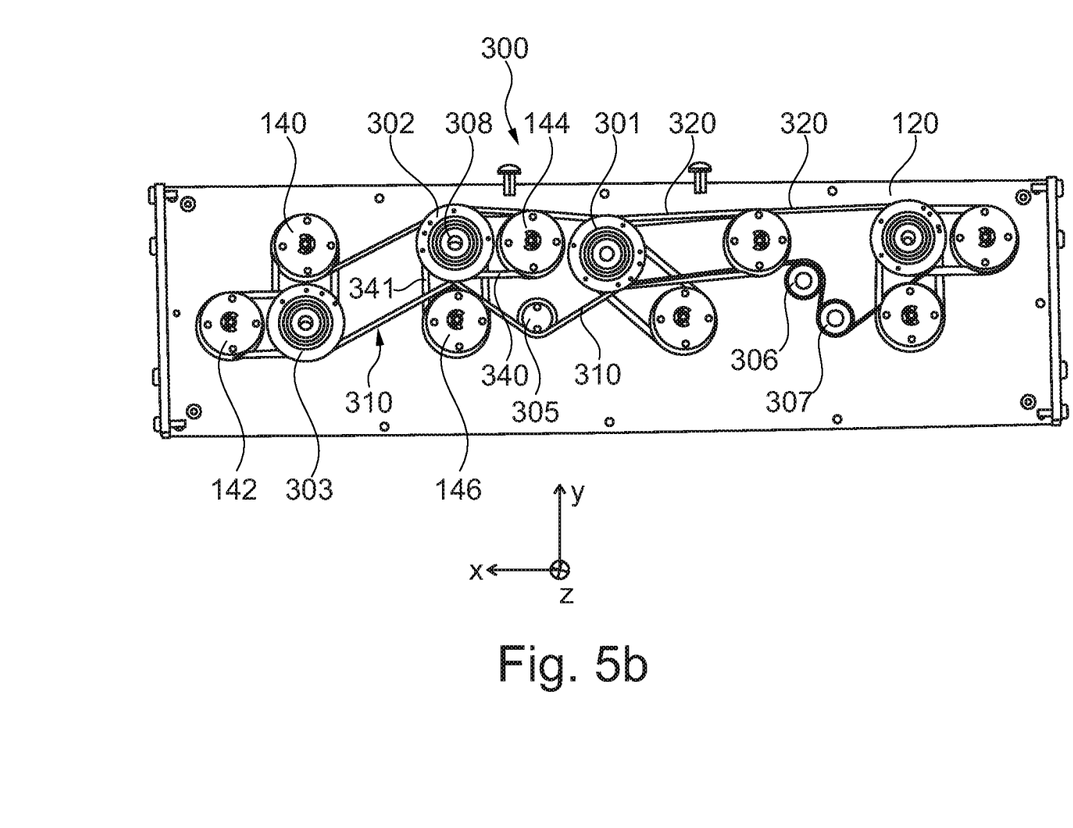
FIG. 5b the drive of FIG. 5a from a changed perspective.

Each shaft element 301-304 is coupled in each case to two coupling elements. Thus for example, the shaft element 302 is coupled to the coupling elements 144 and 146 via in each case a second force transmission element 340 and 341 in the form of a round belt. This is particularly clearly recognisable in FIG. 5b. Thereby, the surfaces of the coupling elements 144 and 148 which are provided with the grooves 148 project out of openings of the housing 120 as is represented for example in FIG. 2. The shaft elements do not project out of the surface through their own openings.

Figure 5C:
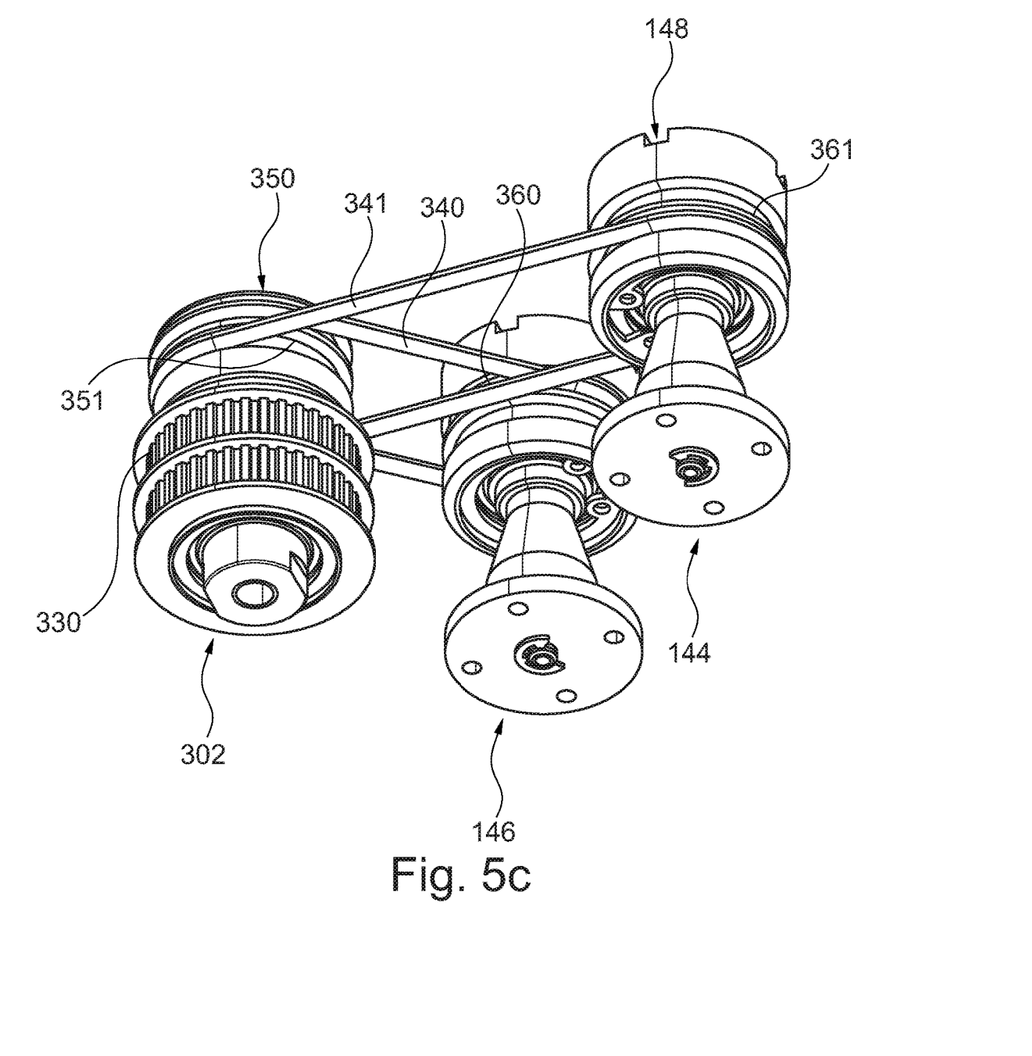

The round belt runs in a recess of the shaft element as well as of the coupling element. This for example is represented in FIG. 5c. The second force transmission element 340 runs in a groove 350 of the shaft element and a groove 360 of the coupling element. The second force transmission element 341 runs in a groove 351 of the shaft element and in a groove 361 of the coupling element. If now the shaft element is set into rotational movement directly via the coupling rod 162 or via a first force transmission element, then the rotation movement of the shaft element is transmitted via the second force transmission elements onto the coupling elements.

As has been described previously, a mechanism of a medical robotics instrument can for example engage into the groove 148 (or a corresponding groove of another coupling element). A movement of the motor, via the coupling rod 162, the shaft elements 301-304 and the second force transmission elements is transmitted onto the coupling elements in this manner, and the distal ends of the instruments 170 and 170' for example are moved, which is to say the shank of the instrument rotates.

In the case that the instrument was moved or rotated in a manner such that the mechanism of the apparatus has reached an abutment, the mechanism of the instrument exerts an movement resistance which can only be overcome by way of applying a very high force. However, this very high force may lead to a damage of the mechanism. The exerted movement resistance of the mechanism of the medical instrument leads to a movement resistance of the coupling element, i.e. the coupling element is prevented from a further rotational movement on account of the mechanism engaging into the groove 148. The friction resistance between the second force transmission element and the coupling element is selected in a manner such that this is smaller than the movement resistance effected by the mechanism of the instrument. Due to this, the round belt slips in the groove and the coupling element executes no further movement. Since in the present embodiment example, a first and a second coupling element are coupled in each case via a second force transmission element to a shaft element, a first coupling element can move independently of the second coupling element in the sense that a slipping-though of the round belt of the first coupling element has no influence on any movement of the second coupling element. In this manner, it is not important for the distal, movable ends of the instruments to be located in a predefined position before inserting into an adapter. If the motor is rotated in each case in one rotation direction for a stretch/distance, which corresponds to the complete rotation scope of the mechanism of the instrument or to the full, maximal rotation scope of the different mechanisms (in each case for moving a different part of the instrument, such as e.g. the rotation of the shank or the oration of the distal end or of different instruments applied into different adapters of the adapter bank) then one can ensure that all instruments applied into an adapter are moved over their compete movement scope, independently of the starting position of the mechanisms of the instrument. Thereby, the mechanisms are temporarily moved simultaneously, i.e. not moved one after the other, as long as the mechanism moved by the coupling element has not yet reached the abutment. If a mechanism reaches the abutment, then the respective coupling element is subjected to a movement resistance and a movement of the shaft element is no longer transmitted onto the coupling element, which in the present embodiment is the round belt which slips through. Mechanisms which have not yet reached the abutment however continue to be moved further. Apart from round belts, further belts can be applied as second force transmission elements, for example flat belts.

After the motor has rotated in a first direction, a rotation movement in the opposite direction is carried out over at least the preceding path/distance. From this point in time, a synchronisation of the movement of the inserted instruments can be ensured. The duration of the first rotation and the subsequent second rotation, i.e. the first and second time periods are selected in a manner such that this is longer than the time which one of the moved mechanisms requires at the given and set speed of the drive, in order to run through its respective complete movement region. Optionally, the duration of the movement in the first or second direction can subsequently be reduced.

With the design of the friction force of the round belt with respect to the coupling element, one should take into consideration the fact that the auxiliary device during the cleaning is located in a fluid which can penetrate into the housing 120 and thus can increase or reduce the movement resistance, from which a slipping through is possible.

In the case of a hydraulic or pneumatic solution, a channel which effects a coupling of the shaft element to the coupling element can comprise a pressure relief valve. If then a mechanism of an instrument exerts a movement resistance onto the coupling element, the pressure in the channel increases and the valve opens on exceeding a pressure.

In the represented embodiment example, thus the movement of the shaft element no longer leads to a movement of the coupling element, since the movement resistance exerted onto the coupling element is too high and exceeds a predefined movement resistance. The predetermined movement resistance is selected in a manner such that a mechanism of an instrument to be cleaned is not damaged.

It is further recognisable in FIG. 5c that a shaft element comprises two toothed belts for in each case one toothed belt or two grooves in each case for a round belt. The number can be varied in each case in other embodiment examples.

Alternatively to the feature that the movement of the shaft element is not transmitted onto the coupling element, it is also to be understood in this application that the coupling element can be functionally divided into two. Thus one can envisage an upper part of the coupling element which can be brought into engagement with the instrument, being coupled to a second part of the coupling element which is coupled to the second force transmission element, in a manner such that when the upper part of the coupling element is subjected to a movement resistance, a movement decoupling of the upper and lower part of the coupling element is effected in the context that both parts continue to be connected to one another (for example via a mounting of the shaft) but can be rotated independently of one another, as soon as the upper part experiences a movement resistance. The upper and the lower part can for example comprises prominences and recesses which correspond to one another in each case (e.g. wave pattern) and which have a positive fit in the direction of the force transmission, wherein the positive fit can be lifted by way of applying a predefined movement resistance, and the two parts can be rotated to one another. For this, the upper and the lower part should be height adjustable with respect to one another, for example along a bearing shaft. The upper and the lower part are thus connected to one another via a coupling, wherein the coupling comprises a no-load running, so that when the upper part is subjected to a movement resistance, the coupling goes over into no-load running and a movement of the upper part is decoupled from the lower part.

Moreover, the feature that the movement of the shaft element is not transmitted onto the coupling element can also be expressed in that a coupling is present between the second force transmission element and the coupling element, said coupling going into no-load running due to the coupling element being subjected to a movement resistance.

Figure 6A:
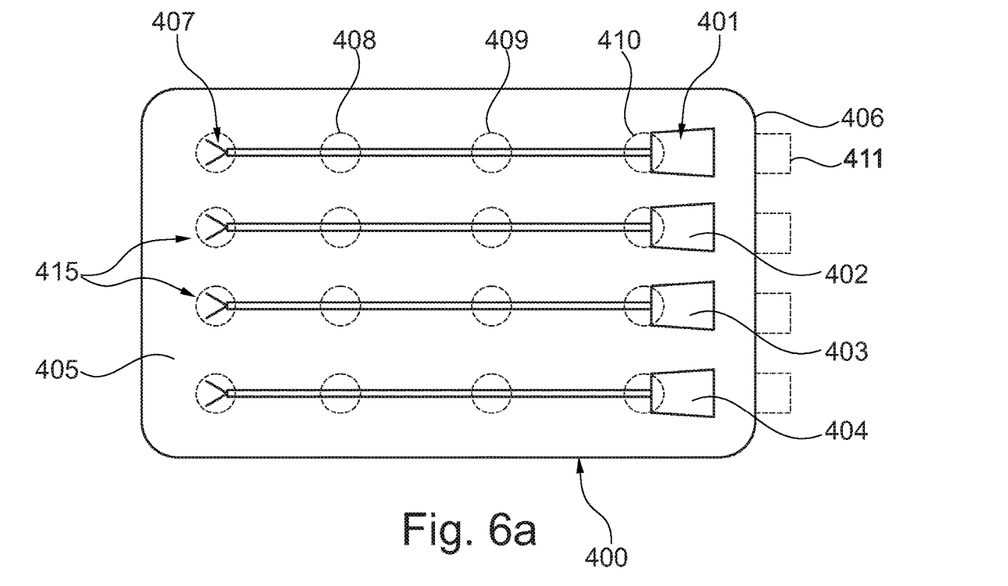
FIG. 6a, 6b examples of an arrangement of sound transducers for subjecting instruments to ultrasound.
Figure 6B:
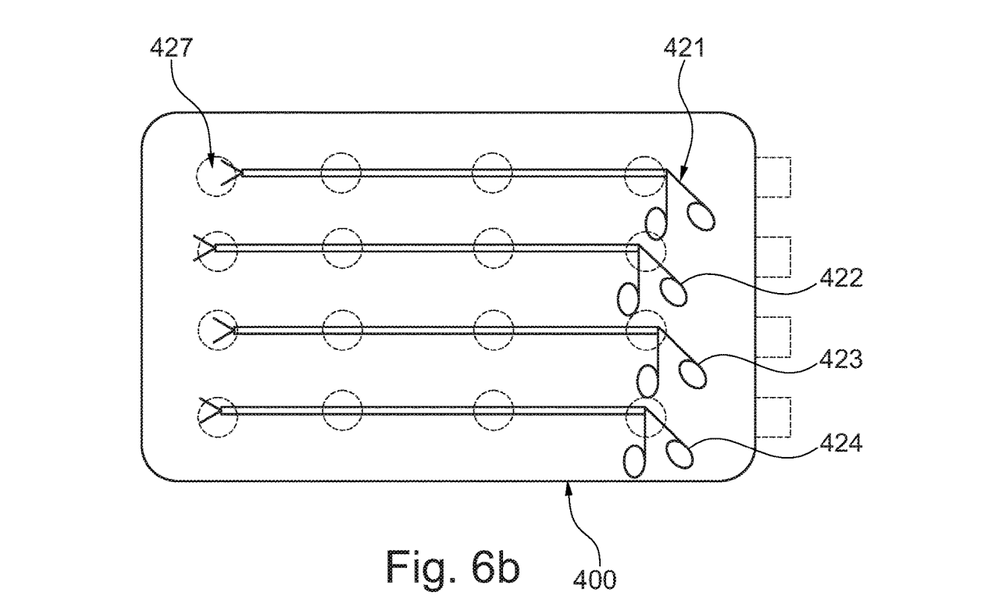

Two tanks for ultrasound cleaning are represented in FIGS. 6a and 6b.

A tank 400, in which a (non-drawn) auxiliary device for fixing medical instruments with four inserted medical instruments 401-404 is arranged is shown in FIG. 6a. For example, with regard to the auxiliary device it can be the case of the auxiliary device 100 described in this application. The position of the instruments 401-404 is defined by the auxiliary device.

Ultrasound transducers 407-411 are drawn in on the tank base 405 and on the tank wall 406. Since the selected view onto the tank is from the outside into the inside of the tank, the ultrasound transducers arranged in the outer side of the tank base and the tank wall are represented in a hatched manner since they actually are not visible from the selected perspective. Thereby the ultrasound transducers 407-410 are located on the tank base and the ultrasound transducer 411 on the tank wall.

The ultrasound transducer 407 is arranged exactly below the distal tip which is to say in the direct vicinity of the distal tip of the instrument 401. The ultrasound transducers 408 and 409 are arranged below the shank of the instrument. The ultrasound transducer 410 is located below the adapter 412 of the instrument. The adapter is moreover subjected to sound by the ultrasound transducer 411 arranged on the tank wall, wherein this transducer is arranged at the height of the instrument, preferably at the height of the rinsing connections of the instrument. Further ultrasound transducers 413 which are arranged analogously to the ultrasound transducers 407-411 are arranged below or at the side of the further instruments 402-404. The distance of the ultrasound transducers 407-410 amongst one another can be uniform.

The tank 400 is represented in FIG. 6b with an alternative auxiliary device (not shown) for mounting holding MIC instruments 421-424. The arrangement of the ultrasound transducers here too is such that at least one ultrasound transducer 427 is arranged in the region of the distal tip of the instrument.

The invention described in this application amongst others includes the following aspects:
1. A drive for the auxiliary device of an ultrasound apparatus, wherein the drive comprises at least one shaft element which is drivable via a first force transmission element, and the shaft element is coupled to at least one coupling element via a second force transmission element, so that a movement can be transmitted from the shaft element onto the at least one coupling element, wherein the second force transmission element is coupled to the at least one coupling element in a manner such that on exceeding a predefined movement resistance of the at least one coupling element, the second force transmission element transmits no movement of the shaft element onto the at least one coupling element.
2. A drive according to aspect 1, wherein the first force transmission element is a first belt, preferably a toothed belt.
3. The drive according to one of the preceding aspects, wherein the second force transmission element is a second belt.
4. A drive according to one of the preceding aspects, wherein at least one first and a second shaft element are present, wherein the first and the second shaft element are coupled via the first force transmission element, so that a movement of the first shaft element can be transmitted onto the second shaft element.
5. A drive according to one of the preceding aspects, wherein a shaft element is coupled to at least one first and a second coupling element via a second force transmission element in each case.
6. A drive according to one of the preceding aspects, wherein the at least one shaft element and the at least one coupling element are arranged in a housing.
7. A drive according to aspect 6, wherein the housing comprises a surface with at least one opening, into which the at least one coupling element projects.
8. A drive according to aspect 6 or 7, wherein the at least one shaft element does not project through the surface.
9. A drive according to one of the preceding aspects, wherein the at least one shaft element and/or the at least one coupling element are designed in a cylinder-shaped manner.
10. A drive according to one of the preceding aspects, wherein the at least one shaft element and/or the at least one coupling element comprise recesses for the first and/or for the second force transmission element.
11. A drive according to one of the preceding aspects, wherein the at least one shaft element and/or the at least one coupling element are rotatably mounted.
12. A drive according to one of the preceding aspects, wherein a force-producing component is coupled to the at least one shaft element, and the force-producing component is preferably a motor.
13. A drive according to one of the preceding aspects, wherein the at least one coupling element on a surface comprises grooves, holes or webs for coupling to a mechanism of a medical robotics instrument.
14. An auxiliary device for a tank of an ultrasound apparatus which comprises a rack and at least one adapter for a medical instrument, wherein the adapter comprises a housing and at least one drive according to one of the preceding aspects, so that a movement of the coupling element effects an active movement of at least one region of the medical instrument.
15. An auxiliary device for a tank of an ultrasound apparatus, which comprises a rack and at least one adapter for a medical instrument, wherein the adapter comprises a housing and at least one coupling element which can be moved with respect to the housing by way of a drive and which can be coupled to the medical instrument, so that a movement of the coupling element effects an active movement of at least one region of the medical instrument.

16. An auxiliary device according to aspect 14 or 15, wherein the adapter comprises a movable fixation device for fixing the medical instrument.

17. An auxiliary device according to one of the aspects 14 to 16, wherein the coupling element comprises a groove on a surface which faces the medial instrument, said groove being for coupling to the medical instrument.

18. An auxiliary device according to one of the preceding aspects 14 to 17, wherein the coupling element is mounted in a resilient manner.

19. An auxiliary device according to one of the preceding aspects 14 to 18, wherein the coupling element can be rotated.

20. An auxiliary device according to one of the preceding aspects 14 to 19, wherein the coupling element is mechanically, hydraulically or pneumatically coupled to the drive.

21. An auxiliary device according to one of the preceding aspects 14 to 20, wherein the rack is designed in a manner such that a force-producing component of the drive is arranged outside the tank, and the at least one adapter is arranged within the tank.

22. An auxiliary device according to one of the preceding aspects 14 to 21, wherein the housing of the adapter is fixed with respect to the rack.

23. An auxiliary device according to one of the preceding aspects 14 to 22, wherein the housing comprises openings and is water-permeable.

24. An auxiliary device according to one of the preceding aspects 14 to 23, wherein a suction and/or pressure rinsing device for rinsing the medical instrument is present, wherein the rinsing device comprises a rinsing adapter for coupling onto the medical instrument and/or a suction and pressure change-over switch.

25. A control and/or operating device for an ultrasound apparatus and for the control of an auxiliary device according to one of the preceding aspects 14 to 24, wherein the control and/or operating device is configured in a manner such that a preferably regular movement of at least one coupling element is effected by the drive.

26. A control and/or operating device according to aspect 25, wherein a rinsing device with a suction and pressure change-over switch is present.

27. A method for the active movement of a region of a medical instrument in a tank of an ultrasound bath, wherein the medical instrument is applied into an adapter and is coupled to a coupling element of the adapter which is movable with respect to the housing, in a manner such that a movement of the coupling element effects an active movement of the region of the medical instrument.

28. A method according to aspect 27, wherein the medical instrument is moved during the subjection of the tank to ultrasound.

29. A method according to one of the aspects 27 or 28, wherein during the active movement of the medical instrument, a fluid of the ultrasound bath is sucked and/or pressed into a cavity of the medical instrument.

The invention claimed is:

1. An auxiliary device for a tank of an ultrasound apparatus, said auxiliary device comprising
a rack and at least one adapter for a medical instrument, the at least one adapter including a housing and at least one coupling element which is movable with respect to the housing by a drive and which can be coupled to the medical instrument so that a movement of the at least one coupling element effects an active movement of at least one region of the medical instrument,
the drive including at least one shaft element driven via a first force transmission element, and
the at least one shaft element being coupled to the at least one coupling element via a second force transmission element so that a movement is transmitted from the at least one shaft element onto the at least one coupling element,
the second force transmission element being coupled to the at least one coupling element in a manner such that on exceeding a predefined movement resistance of the at least one coupling element, the second force transmission element transmits no movement of the at least one shaft element onto the at least one coupling element.

2. The auxiliary device according to claim 1, wherein the at least one adapter includes two or more of the coupling elements which are each respectively connected to two of the second force transmission elements, wherein the drive is configured in a manner such that the respective second force transmission elements are simultaneously movable by the drive.

3. The auxiliary device according to claim 2, wherein the adapter includes a movable fixation device for fixing the medical instrument.

4. The auxiliary device according to claim 2, wherein at least one of the coupling elements on a surface facing the medical instrument includes a groove for coupling onto the medical instrument.

5. The auxiliary device according to claim 2, wherein at least one of the coupling elements is mechanically, hydraulically or pneumatically coupled to the drive.

6. The auxiliary device according to claim 2, wherein the rack is configured such that a force-producing component of the drive is arranged outside of the tank, and the at least one adapter within the tank.

7. The auxiliary device according to claim 2, wherein a suction and/or a pressure rinsing device is present for rinsing the medical instrument, wherein the suction and/or pressure rinsing device includes a rinsing adapter for coupling onto the medical instrument and/or onto a suction and pressure change-over switch.

8. The control and/or operating device for an ultrasound apparatus and for the control of an auxiliary device according to claim 2, wherein the control and/or operating device is configured in a manner such that a regular movement of the at least one coupling element is effected by the drive.

9. The control and/or operating device according to claim 8, wherein a rinsing device with a suction and pressure change-over switch is present.

10. The control and/or operating device according to claim 8, which is configured in a manner such that the drive for a first time period is moved in a first direction and subsequently for a second time period in a second direction which is opposite to the first direction, wherein the first and the second time period are selected in a manner such that these are longer than a time period which is necessary for running through a complete movement region of a coupled instrument.

11. The control and/or operating device according to claim 10, wherein the movement in the first and second direction is effected regularly in a consecutive manner over the first and the second time period respectively.

12. A method for the active movement of at least one region of a medical instrument in a tank of an ultrasound bath, wherein the medical instrument is applied into an adapter and is coupled to a coupling element of the adapter which is movable with respect to the housing, one of two or more coupling elements is coupled to a mechanism of the medical instrument, in a manner such that a movement of the coupling element, of the two or more coupling elements effects an active movement of the at least one mechanism of the medical instrument.

13. The method according to claim 12, wherein the medical instrument is moved during the subjection of the tank to ultrasound.

14. The method according to claim 12, wherein a fluid of the ultrasound bath is sucked and/or pressed into a cavity of the medical instrument during the active movement of the medical instrument.

15. The method according to claim 12, wherein the medical instrument is applied into an adapter and is coupled to a coupling element of the adapter which is movable with respect to the housing by a drive, wherein the drive for the duration of a first time period is rotated in a first direction and subsequently for a second time period in a second direction which is opposite to the first direction, wherein the first and the second time period is selected in a manner such that this lasts longer than the time, in which a complete movement region of the coupled mechanism is run through.

* * * * *